United States Patent [19]
Müller-Derlich et al.

[11] Patent Number: 6,030,614
[45] Date of Patent: Feb. 29, 2000

[54] AMELIORATING IMMUNOLOGICAL REJECTION OF ALLOGRAFT

[75] Inventors: Jutta Müller-Derlich, Germering; Robert Koll, Kirchheim; Wolfgang Böhm, Munchen; Franz A. Bieber, Unterschleissheim; Reiner Spaethe, Starnberg, all of Germany

[73] Assignee: Plasmaselect GmbH Teterow, Germany

[21] Appl. No.: 08/632,695

[22] Filed: Apr. 16, 1996

Related U.S. Application Data

[63] Continuation of application No. 08/373,343, Jan. 17, 1995, abandoned, which is a continuation-in-part of application No. 08/242,489, May 13, 1994, abandoned.

[51] Int. Cl.$^7$ .................. A61K 39/395; C07K 16/28
[52] U.S. Cl. .................. 424/140.1; 424/153.1; 424/156.1; 424/173.1; 424/145.1; 424/158.1; 424/93.71; 435/70.21; 435/69.6; 530/387.1; 530/388.2; 530/388.25
[58] Field of Search .................. 424/140.1, 153.1, 424/156.1, 173.1, 145.1, 158.1, 93.71; 435/70.21, 172.2, 69.6; 530/387.1, 388.2, 388.25

[56] References Cited

U.S. PATENT DOCUMENTS 5,560,911  10/1996  Koren et al. .................. 424/131.1

OTHER PUBLICATIONS

Bannett et al. (1987) Transplantation Procedings. vol. 19 No. 6: 4543–4546.

du Moulin et al. (1993) Blood Purif. vol. 11: 145–149.

Palmer et al. (1989). The Lancet Jan. 7, 1989 p. 10–12.

Euler et al. (1992) Transfus. Sci. vol. 13: 167–184.

Morrison (1992) Ann. Revs. Imunvol. vol. 10 239–265.

The Lancet Aug. 25 1990 Editonal: Consensus on Ivig. p. 470–471.

*Primary Examiner*—Julie Burke
*Attorney, Agent, or Firm*—Seed and Berry LLP

[57] ABSTRACT

The invention provides a method to prevent or ameliorate hyperacute or acute rejection of a human donor organ transplanted to a human recipient. Hyperacute rejection would normally occur after a human subject receives a transplanted human organ against which the subject has preformed anti-HLA antibodies. Acute rejection occurs when the recipient of a human organ forms antibodies against that organ after transplant. The invention method comprises passing the plasma of the recipient over a sterile and pyrogen-free column coupled to anti-human immunoglobulin antibodies which bind to and remove a significant portion of the immunoglobulin from the subject's plasma.

20 Claims, 7 Drawing Sheets

AMELIORATING IMMUNOLOGICAL REJECTION OF ALLOGRAFT

CROSS-REFERENCE TO RELATED APPLICATION

This application is a continuation application of U.S. Ser. No. 08/373,343, filed Jan. 17, 1995, now abandoned, which is a continuation-in-part of U.S. Serial Number 08/242,489, filed May 13, 1994, now abandoned.

TECHNICAL FIELD

The present invention is in the general field of transplantation of immunologically incompatible organs. Specifically, the invention relates to methods for the removal of antibodies from the blood of human recipients to prevent immunological rejection of a transplanted human organ. The invention also relates to methods for preparing human immunoglobulin-depleted plasma suitable for infusion to human subjects in need of such plasma.

BACKGROUND

There is a great need world-wide for transplantable organs such as heart, kidney, liver, and pancreas. In the case of a single kidney or a partial pancreas transplant, it is sometimes possible to locate a living donor with immunological markers compatible with the transplant recipient, although organ donation by a living donor involves great risk and possible deleterious health effects for the donor. In all other cases, the organ donation must come from a high quality, heart-beating human cadaver, and again there must be a good immunological match between the donor and the recipient. Patients in need of an organ transplant often must be on a waiting list for longer than one year, and many patients die before a suitable organ becomes available.

The term "HLA" stands for Human Leucocyte Antigens which are expressed on the surface of most blood and tissue cells. Every person has a set of six HLA antigens which define his tissue type. Anti-HLA antibodies against foreign HLA antigens are acquired by a patient through multiple blood transfusions and pregnancies. These cytotoxic antibodies can cause hyperacute rejection of a transplanted organ despite immunosuppressive therapy.

If the recipient of a transplanted organ has cytotoxic anti-HLA antibodies against the tissue of the donor organ, hyperacute rejection of the donor organ follows within minutes to 48 hours after transplant. Hyperacute rejection normally occurs after transplants of certain types of immunologically mismatched allografts (human to human) and xeno-grafts (animal to human).

In choosing a suitable organ for transplant to a human subject, every attempt is made to locate a human donor organ having an ABO blood type and HLA haplotypes which match those of the recipient. Thus, the recipient is not expected to have cytotoxic anti-HLA antibodies against these potentially antigenic molecules, since they are self-antigens. However, a small number of patients in need of organ transplant carry cytotoxic anti-HLA antibodies against several HLA molecules, sometimes including their own HLA molecules. These patients are known as "sensitized" or "hyper-sensitized". Often, a sensitized patient has antibodies against so many different HLA molecules that it is not possible to locate a donor organ that would not be in danger of hyperacute rejection.

The "hyperacute rejection reaction" occurs when the recipient's immune system attacks and destroys the transplanted organ within minutes to hours, typically within 48 hours after transplant. Even when the recipient receives immunosuppressive therapy, hyperacute rejection is not ameliorated.

The hyperacute rejection reaction is thought to occur as a result of pre-formed antibodies in the blood of the recipient which recognize and bind to antigens in the tissue of the donor organ once the transplanted organ is in place and is perfused with the blood of the recipient. When the antibodies bind to endothelial cells of the donor organ blood vessels, they stimulate the deposition of complement proteins, which also originate from the blood of the recipient. Antibody/complement deposition is thought to initiate the "classical" pathway of complement action, which ultimately leads to disruption of the endothelial cell lining of the blood vessels of the donor organ (In: *Immunology*, Eds: Roitt, I. M., et al, J.B. Lippincott Co, Philadelphia, 1989, Chapter 13, pages 13.1–13.16). The hyperacute rejection reaction results in a necrotic donor organ within minutes to hours after xenotransplant. It has been hypothesized that necrosis of the donor organ results from "activation" of its endothelial cells, which in turn leads to interstitial hemorrhage, inflammation, edema, and small vessel thrombosis (Platt, J. L., et al., *Immunology Today* 11:450–456, 1990).

An analogy to the hyperacute rejection reaction can be seen in the transplant of ABO-mismatched organs from human donor to human recipient. A recipient with type O blood, for instance, is expected to have preformed anti-A and anti-B antibodies in his blood. Usually, every attempt is made to locate a donor organ well-matched for both ABO blood type and HLA haplotype. However, in certain situations, an ABO-mismatched organ from an HLA-matched donor is the best or only organ available for transplant. In attempts to prevent hyperacute rejection when ABO-mismatched organs were transplanted, pre-formed anti-A/anti-B antibodies were removed from the recipients' blood using extracorporeal perfusion of the recipients' plasma over synthetic A/B blood group antigens covalently linked to silica. Successful kidney and bone marrow transplants were reported using this procedure (Bannett, A. D., et al., *Transplant. Proc.* 1987 XIX:4543–4546; Bensinger, W. I., et al., *Transplantation* 1982 33:427–429; U.S. Pat. No: 4,137,401; European patent no: 89311540.2).

It was found that certain pre-formed antibodies in humans bind to carbohydrate residues on foreign antigens. In particular, the antigenic blood group substances A and B bear trisaccharides, which have been chemically synthesized. In a baboon/baboon model for ABO-mismatched heart transplant, the recipient was first administered intravenous A or B trisaccharide on the theory that the trisaccharide would form a "neutralizing" complex with the preformed anti-A or anti-B antibody, thereby preventing hyperacute rejection. When continuous A/B antigen treatment was combined with high-dose immunosuppression, hyperacute rejection was ameliorated in the majority of experiments (Cooper, D. K. C., et al., *Transplant. Proc.* 24:566–571, 1992).

It has been proposed that immunoglobulins be removed from the blood of an organ recipient when hyperacute rejection of the transplanted organ would otherwise be expected to occur. Immunoglobulin can be removed non-specifically by plasmapheresis. Conventional plasmapheresis, or plasma exchange, results in loss of blood volume, recipient sensitization, and activation of the complement and clotting systems. These side effects of plasmapheresis are somewhat alleviated by volume replacement with pooled preparations of fresh frozen plasma, human albumin, immunoglobulin, and/or a type of bulking agent such as starch. Coagulation factors, platelets, and anti-thrombotic factors must also be replaced. This treatment carries the risk of virus transfer from the pooled human preparations, as well as the risk of anaphylactic reaction to foreign substances. Plasmapheresis does not appear to be either practical or safe for immediate pre-transplant or post-transplant use because of the risk of excessive bleeding.

There has been considerable interest in non-specific antibody removal for indications other than organ transplant, mainly. for the treatment of autoimmune disease. One method for non-specific antibody removal involves perfusing the autoimmune subject's plasma over a column coupled with Protein A from *Staphylococcus aureus*. Protein A, a major component of the cell wall of *S. aureus*, has a high affinity for a portion of the Fc-region of sub-classes 1, 2, and 4 of immunoglobulin G ($IgG_1$, $IgG_2$, $IgG_4$) (Dantal, J., et al., *New England J. Med.*550:7–14, 1994; Nilsson, I. M., et al., *Blood* 58:38–44, 1981; Palmer, A., et al., *The Lancet* Jan. 7, 1989, pp.10–12). The Protein-A coupled columns have also been used for the non-specific removal of anti-HLA antibodies from hypersensitized patients who are in need of a kidney transplant. These patients typically suffer from idiopathic nephrotic syndrome (INS). They commonly suffer a relapse of INS soon after transplantation of even the most well-matched donor kidney, thus practically excluding them from the possibility of having any kind of currently available kidney transplant. The efficacy of the Protein A column treatment in several INS patients after kidney transplant was reported (Dantal,et al, supra; Palmer, et al., supra).

It has been proposed to treat autoimmune disease by removal of a significant portion of the patient's immunoglobulins using a column coupled to antibodies directed against human immunoglobulin. Use of such columns in the treatment of auto-immune disease has been suggested as follows: Müller-Derlich, J., et al., *Artificial Organs* 17 (6):abs. 330 and 339, June 1993; Müller-Derlich, J., et al., *Transfusion Medicine* 3 (suppl.1):abs. PS20, September 1993; Müller-Derlich, J., et al. *Immunobiology* 189 (1–2): p.237, Abs. R.9, Sep. 30–Oct. 2, 1993; du Moulin, A., et al., *Blood Purif* 11:145–149, 1993 (library receipt date=Nov. 17, 1993); Koll, R. et al, 23. *CONGRESS OF THE INTERNATIONAL SOCIETY OF BLOOD TRANSFUSION, Jul. 3–8, 1994,* Amsterdam-Rai.

It has been proposed that, even if antibodies were removed from the recipient's blood, it would still be necessary to inactivate or remove complement to prevent a hyperacute rejection reaction after transplanting a human organ in danger of being hyperacutely rejected. The administration of cobra venom factor can accomplish the depletion of complement activity by a massive activation of C3, which proceeds to exhaust all subsequent components in the complement cascade. However, the effectiveness of cobra venom factor is short-lived because the recipient rapidly forms neutralizing antibodies against the factor. The administration of cobra venom factor also carries the risk of anaphylactic reaction to the foreign substance.

If the hyperacute rejection phenonenon could be prevented in the early days following transplant, there is a good chance that the patient's immune system would undergo a process of "accommodation" which would diminish or eliminate the reaction between the antibodies and complement of the patient with the endothelial cells of the donor organ (Bach, F. H. et al., *Transplant Proc.* 23:205–207, 1991.

Another type of organ rejection is observed when the recipient does not have cytotoxic antibodies against the donor organ, but develops antibodies against the foreign tissue over the course of weeks to months after transplant. This would normally occur if, for instance, an HLA-mismatched human organ were transplanted to a human recipient. The newly formed antibodies would cause rejection of the organ in much the same fashion as cytotoxic anti-HLA antibodies cause hyperacute rejection, but the delayed rejection phenomenon is known as "acute rejection".

What is needed is a method to prevent or ameliorate the severity of the hyperacute rejection reaction or acute rejection reaction in the transplantation of a human organ to a human subject who has formed antibodies against the donor organ.

SUMMARY OF THE INVENTION

The invention provides a method for preventing or ameliorating hyperacute or acute rejection of a human donor organ transplanted to a human recipient. The method of the invention is suitable for use in human subjects because all materials used are sterile and pyrogen-free.

The invention method requires immunoapheresis (IA) using a sterile and pyrogen-free column coupled to antibodies which bind to human immunoglobulin. In immunoapheresis, the recipient's plasma is perfused over the column, thereby removing immunoglobulin and circulating immune complexes, and the immunoglobulin-depleted plasma is replaced to the recipient.

The term immunoapheresis (IA) refers to the immunoapheresis treatment described herein which is performed using the antibody-coupled columns provided in co-owned patent application U.S. Ser. No. 08/242,215, which is herein incorporated by reference.

The method is applied to prevent or ameliorate a hyperacute rejection reaction which would normally occur in a human recipient of a human donor organ when the recipient has cytotoxic anti-HLA antibodies against antigens in the donor organ. First, the intended organ recipient is subjected to at least three rounds of IA, then the donor human organ is transplanted to the recipient, and thereafter the recipient is provided with further rounds of IA as well as an immunosuppressive and/or cytotoxic regimen. Optionally, the intended recipient is given a pulse of immunosuppressive agent after the first rounds of IA, and before transplant.

The method to prevent or ameliorate acute rejection comprises subjecting the human organ recipient to succeeding rounds of IA in combination with an immunosuppressive regimen.

The invention also provides methods to determine whether a prospective donor organ would be suitable for transplant to a prospective human recipient having cytotoxic anti-HLA antibodies if the recipient first receives IA. A plasma sample for cross-matching is drawn immediately after the first series of IA treatments. Alternatively, a plasma sample drawn from a simple blood sample of the prospective recipient is subjected to the IA column treatment in vitro. Thereafter, the immunoglobulin-depleted sample is subjected to cross-matches with lymphocytes from prospective donors.

The invention also provides a method to produce immunoglobulin-depleted human plasma which is useful for plasma replacement to patients in need of such plasma because of conditions such as auto-immune disease or immunological rejection of organ transplant.

It is the primary object of this invention to provide a method to prevent or ameliorate hyperacute or acute rejection of a human donor organ transplanted to a human recipient.

It is also an object of this invention to provide a method to prevent or ameliorate the hyperacute rejection reaction which normally occurs upon transplantation of a donor organ to a human patient who has pre-formed anti-HLA antibodies against the donor organ tissue.

It is a further object of this invention to provide a method to prevent or ameliorate an acute rejection of a transplanted organ after transplantation.

It is a further object of this invention to provide a method to determine the suitability of a prospective donor organ for transplant to a prospective recipient, after IA treatment. Typically, the prospective recipient has cytotoxic anti-HLA antibodies which, without IA treatment, would nullify the chances of finding a suitable donor organ.

It is a further object of this invention to provide a method to produce immunoglobulin-depleted human plasma, suitable for use in human subjects in need of such plasma.

DETAILED DESCRIPTION OF THE INVENTION

Figure 1:
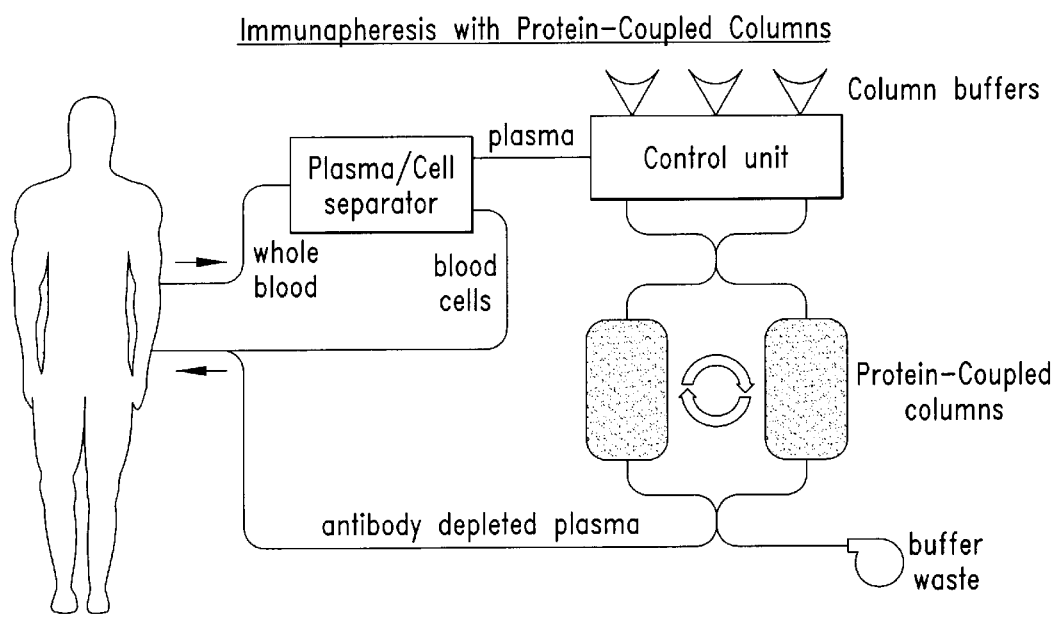
FIG. 1 illustrates the aseptic connections from the subject's bloodstream, to the plasmapheresis machine, over the column, and back to the subject.

Transplantation of a donor organ to a human who has cytotoxic anti-HLA antibodies against the organ will normally lead to hyperacute rejection of the organ within a few minutes to 48 hours. The principle clinical features of hyperacute rejection of a transplanted kidney, for instance, are a sudden drop in urine output accompanied by a sharp increase in serum creatinine levels. The hyperacute rejection reaction is thought to be largely due to cytotoxic anti-HLA antibodies in the blood of the recipient which bind to antigens on the endothelial cells of the blood vessels of the transplanted organ, thereby activating complement, disrupting the endothelial cell lining, and causing necrosis of the donor organ.

Another type of immunological rejection, known as "acute rejection" occurs after transplant of an immunologically mismatched organ against which the recipient has no preformed antibodies, but against which the recipient forms antibodies days to weeks after transplant. This delayed type of rejection reaction shares at least one feature of the hyperacute rejection reaction, namely its partial causation by antibodies against the donor organ tissue.

The present invention provides a method to prevent or ameliorate hyperacute or acute rejection by subjecting the intended recipient to several rounds of immunoapheresis (IA).

IA involves separating the human subject's plasma from cells and platelets and perfusing the subject's plasma over a sterile and pyrogen-free column coupled to antibodies which bind to human immunoglobulin, thereby removing immunoglobulin from the recipient's plasma. The subject's immunoglobulin-depleted plasma is remixed with his blood cells and platelets, and the reconstituted blood is returned to the recipient.

Methods and compositions for the production of sterile and pyrogen-free protein coupled columns are provided herein in Examples 3–7.

For each individual IA procedure, the subject's separated plasma is continuously passaged over the sterile and pyrogen-free antibody-coupled column, and the column effluent is returned to the subject for at least 2–3 plasma volumes. This treatment effects the removal of a significant portion of the immunoglobulin from the subject's plasma. Thus, IA treament preferably results in a reduction of total IgG of at least about 60% to about 99%, more preferably at least about 85% to about 99% or greater, as compared with total IgG levels prior to any IA treatment. This treatment also preferably results in a significant reduction of total IgM of at least about 50% to about 99%, more preferably at least about 60% to about 99% or greater, as compared with total IgM levels prior to any IA treatment. It is expected that the treatment can reduce total IgM and/or IgG below the sensitivity level of a standard immunoglobulin assay, thus the assay results may indicate no detectable IgM and/or IgG remaining after treatment.

The sterile and pyrogen-free column is preferably coupled to antibodies which bind to both human IgG and human IgM. The coupled antibodies can be pooled polyclonal antibodies raised in animals such as sheep immunized with pooled human immunoglobulins plus adjuvant. Preferably, the coupled antibodies bind to human light chains such as lambda and kappa light chains, and thereby recognize and bind to both human IgG and IgM. Most preferably, the coupled antibodies also bind to IgG heavy chain. Alternatively, the coupled antibodies may be monoclonal or recombinant antibodies which bind to human immunoglobulins.

Fortunately, it was discovered that a human subject can tolerate very well the removal of the majority of both IgG and IgM antibodies over several days pre- and post-transplant. Suitably, the IA procedure results in no significant reduction in plasma coagulation factors, i.e. no reduction in fibrinogen, Factor V or Factor VIII levels. However, to help prevent infections, it is strongly recommended that after two or three IA sessions a preparation of human immunoglobulin be administered ("IVIG", for instance Gammagard®, Baxter Hyland). The administration of IVIG may also help inhibit antibody production through a negative feedback mechanism exerted by the antibodies within the IVIG preparation on plasma cells of the recipient. The administration of IVIG may also exert various immunomodulatory effects induced, for example, by anti-idiotypic antibodies of the IVIG preparation, or by interference with $F_c$-receptors on immunocompetent cells. The scientific literature provides a multitude of hypotheses on the immunomodulatory properties of IVIG. However, there is a growing body of evidence showing that IVIG decreases or even inhibits antibody production, masks antibodies, or induces tolerance. The present inventors found that in vitro mixing of Gammagard® with serum from a dialysis patient having a high panel reactivity to anti-HLA antibodies reduced the cytotoxicity of the anti-HLA antibodies in the sample (data not shown). Subsequently, it was found that $F(ab)_2$- fragments prepared from Gammagard® by enzymatic cleavage reproduced the results, suggesting that the activity in Gammagard® was anti-idiotypic in nature. Moreover, increasing the ratio of Gammagard® to anti-HLA antibodies prior to mixing increased the reduction in cytotoxicity, indicating a dose-dependent effect in vitro (data not shown).

To specifically prevent or ameliorate hyperacute rejection, the passage of 2–3 volumes of the intended recipient's plasma over the column is repeated once per day on at least 3 different days over a period of 3–5 days pre-transplant. This IA treatment greatly reduces the amount of circulating immunoglobulins and immune complexes in the patient's blood. After the donor organ is transplanted, the recipient is provided with additional rounds of IA combined with immunosuppressive therapy.

Optionally, a pulse of an immunosuppressive agent may be administered after at least 3 rounds of IA, and before transplant. Herein, the term "immunosuppressive agent" refers to anti-mitotic/cytotoxic drugs such as cyclophosphamide, cyclosporin A, antibodies against lymphocytes, vaccines, and other drugs which inhibit the proliferation, differentiation, or antibody synthesis in cells of the immune system. Herein the term "pulse of immunosuppressive agent" refers to an infusion of a single dose of the agent.

Thereafter, the donor organ is transplanted to the patient. The timing of the transplant is based on (1) availability of suitable organ, (2) intended recipient's medical condition and lab values, and (3) type of immunosuppressive agent administered, if any. If the agent given as a pulse is known to exhibit nephrotoxicity (like cyclophosphamide does), transplantation is delayed until the serum concentration of the agent has declined in order to reduce risk for the function of the transplanted kidney. In the case of a cyclophosphamide pulse, transplant should be delayed for about 3 days after the pulse. In general, the interval between the immunosuppressive pulse and transplant is chosen depending on the type of organ to be transplanted, the known effects of the agent on that organ, and the clearance of the agent from the recipient's body.

In theory, the organ transplant may be performed shortly after at least three rounds of IA and the optional pulse of immunosuppressive agent. In practice, however, the transplant must often be delayed for as long as 50–80 days or longer until a suitable donor organ becomes available. If it is desired to keep the HLA titers low during the waiting period, IA may be performed at intervals. An immunosuppressive regimen may also be maintained during the waiting period, at the discretion of the responsible physician.

In order to aid in the selection of a suitable donor organ, a plasma sample is drawn from the intended recipient's circulation immediately after the first series of IA treatments and then subjected to cross-matching with lymphocytes from the prospective donor. Alternatively, a sample of the intended recipient's plasma derived from a simple blood sample may be passed over the column of the invention in vitro, and then subjected to cross-matching. It is anticipated that in vitro column treatment of a simple blood sample may spare the patient repeated IA treatments while awaiting a suitable donor organ. Cross-matching of the patient's column-treated plasma can be continually conducted with lymphocytes of prospective organ donors. Then, as soon as a suitable organ is identified, the patient can immediately start the pre-transplant IA treatments.

Post-transplantation, the IA procedure is repeated on at least three different days per week, preferably three times per week for the two weeks following transplant. The decision to repeat the IA procedure after the sixth procedure is suitably based on a monitoring of organ function, anti-HLA antibody titers, serum creatinine, and biopsy of the grafted organ. In the case of kidney transplant, the IA procedure is repeated if there is a rise in anti-HLA antibody titer in conjunction with a decrease in urine output, an unexplained rise in serum creatinine (i.e. not a drug side-effect), and/or a graft biopsy showing signs of hyperacute rejection.

When anti-donor organ specific antibody titers begin to rise post-operatively without other signs of organ rejection, that is an indication that "accommodation" of the recipient's immune system may be occurring, and that the danger of hyperacute graft rejection is probably past. At this point, the column procedure does not have to be repeated, and the subject may be maintained on conventional immunosuppressive therapy.

Another type of immunological rejection, which occurs days to weeks after organ transplant, can also be prevented or ameliorated by the IA treatment. In this case, an immunologically mismatched human organ is transplanted to a human recipient who does not yet have antibodies formed against this donor organ tissue. However, since the donor organ has antigens which are not recognized as "self-antigens" by the immune system of the recipient, the recipient will develop antigens against the donor organ tissue over time. The newly developed anti-donor antibodies will bind to the donor organ endothelial tissue antigens and activate complement, leading to necrosis of the donor organ. Preferably, in this case, the organ recipient is monitored for early signs of rising antibody titer and/or organ rejection, and the recipient's blood is processed by the method of the invention (IA) to remove immunoglobulin, including anti-donor organ immunoglobulin.

The present inventors propose that the effectiveness of the invention is based on the following hypothesis:

(1) immunoapheresis (IA) causes dose-dependent reduction of circulating immunoglobulins (Ig) and immune complexes (shown here); then, (2) the reduction of circulating Ig causes stimulation of antibody-producing memory B cells to enter mitosis (Euler, H. H., et al., *Transfus Sci* 13:167–184,1992); then, (3) the memory B cells entering mitosis are specifically killed by a pulse of immunosuppressive agent, and (4) plasma cells are inhibited in their production of anti-HLA antibodies by an infusion of a preparation of human Ig (IVIG); then (5) the level of anti-HLA antibodies in the patient's blood is greatly reduced, such that, (6) a rejection reaction is not mounted against the HLA antigens in the donor organ.

It is expected that follow-up treatment of a human organ transplant recipient may include standard long-term immunosuppressive therapy, such as administration of a steroid such as Prednisone™, anti-proliferative drugs such as Azothioprine™, and/or anti-T-lymphocytic drugs such as cyclosporine. However, the method of the invention allows a transplanted organ to survive the initial post-operative period during which hyperacute rejection would otherwise occur, thereby making organ transplant to a sensitized or hyper-sensitized individual feasible.

The IA procedure of the present invention is also expected to aid the survival of a donor organ when the recipient produces antibodies at a later stage after transplant.

The IA procedure of the present invention can also be used in vitro to remove immunoglobulin from donated human plasma. The immunoglobulin-depleted plasma can then be used in transfusions for transplant patients or other patients in need of such plasma.

The following experimental examples are offered by way of illustrating the invention and are not intended to limit the scope of the claims in the invention.

EXAMPLE 1

Removal of immunoglobulin from the blood of human subjects.

Anti-human immunoglobulin coupled columns were used for the removal of immunoglobulin from the blood of human patients suffering from idiopathic thrombocytopenic purpura (ITP), systemic lupus erythematosus (SLE), vasculitis, and sensitizatiion to HLA. These procedures were part of clinical trials carried out in Europe for the treatment of autoimmune patients whose conditions were refractory to conventional treatments, and patients in need of kidney transplant who had cytotoxic anti-HLA antibodies in their blood.

The overall system for immunoglobulin depletion is shown in FIG. 1. Briefly, the tubing system of the primary separation system was first filled with sterile 0.9% NaCl. Two anti-human Ig columns (Ig-Therasorb™, Baxter, Immunotherapy Division, Europe) were connected with the primary separation system as shown (FIG. 1). All tubing connections were made under aseptic conditions.

To remove the preservative solution from the columns (310 or 150 ml volume), each column was rinsed before its first use with 5 liters sterile 0.9% NaCl solution, at a flow rate of 90–100 ml/min. For each subsequent use, it was sufficient to rinse each column with 2 liters of the sterile solution, at the same flow rate.

Before start of the procedure, the entire system was tested for absence of air bubbles and leaks, correct connections of the solutions, including the anticoagulants, correct installation of the programming of the device, functionality of the automatic clamps, and the safety system.

The appropriate canulae were connected to the left and right cubital veins of the patient. Blood samples were taken. The connection to the blood cell separator was put in place.

Anticoagulation was accomplished with either heparin and/or citrate (ACD-A or ACD-B). When citrate was the anti-coagulant, during the first half of the procedure, the citrate was used at a dilution of 1:22 to 1:18. In the second therapy phase, the dilution utilized was 1:12 to 1:8. Symptoms of hypocalcemia were monitored (paraesthesia in fingers or lips), and the administration of citrate was diminished accordingly. Calcium tablets could be given in cases of frank hypocalcemia.

After the venous puncture and the connection of the tubing system to the patient, the blood cell separator was filled with the patient's blood. The blood flow rate was kept between 50–90 ml/min. When a column with a volume of 100 ml was used, the liquid level was maintained at about 0.8 cm over the Sepharose™ in the column. After the stabilization of the separation process, the cell-free plasma was directed through the tubing system over the first column. It was important to keep the flow rate even and to monitor the plasma level over the Sepharose™ in the column. A higher plasma level was undesirable, because it would have led to a higher volume burden for the patient, and plasma loss due to plasma retention in the column.

Using a plasma flow rate of up to 40 ml/min, the column was loaded with as much plasma as possible during 15 minutes. Thereafter, the plasma flow was switched to the second column, which was likewise filled with as much plasma as possible in 15 minutes.

During the time of filling of the second column, the plasma in the first column was flushed out using sterile 0.9% NaCl at the plasma flow rate. One column volume of plasma was returned to the patient together with the blood cells which had been removed.

Also during filling of the second column, the first column was regenerated as follows: (1) A further rinse with 50 ml 0.9% NaCl at a flow rate of 100 ml/min; (2) Desorption of the bound immunoglobulin with one column volume of sterile 0.2 M glycine/HCl buffer, pH 2.8. The controller of the device prevented contact between this solution and the patient. The desorbed immunoglobulin was discarded. (3) Neutralization with one column volume of sterile PBS., pH 7.4. Testing of the neutralization using litmus paper. (4) Rinsing out of the PBS with at least one column volume of sterile 0.9% Nacl. The column was then ready for the next round of adsorption.

Then, the filling of the columns was again automatically switched. This procedure was repeated as many times as necessary to process the desired volume of plasma. The number of cycles used was chosen by the attending physician, according to the condition and needs of the patient. So far, within the inventors' clinical experience, it has been possible to process up to 3.5 times the extracorporeal volume of a given patient during one column procedure. Moreover, the number of cycles used was not limited by the binding capacity of the columns, but rather by the needs of the individual patient.

Blood samples were taken for analysis of the success of the procedure. Concentrations of IgG, IgM, IgA, and IgG subclasses were determined by radial immunodiffusion or nephelometry before and after apheresis.

Panel reactivity (PR) tests were done for those patients who had anti-HLA antibodies. For the PR test, the patient's serum was added to each well of a microtiter plate which contains different HLA-typed cells. If the patient serum contains cytotoxic anti-HLA antiodies, complement mediated lysis occurs. A PR value of 50% is achieved if half of the wells contain lysed cells. Distribution and frequency of HLA antigens presented in this lympocyte panel were characteristic of the prospective organ donor pool. Thus, the higher the PR value, the smaller the chance that a well-matched donor organ could be found in an acceptable period of time.

After each procedure, the columns assigned to each patient were regenerated and stored under aseptic conditions at 2–8° C. until the next use for the same patient.

Results: The IgG concentration in the subjects' blood was reduced by at least 70% to over 99% compared to starting concentrations. IgA and IgM levels were reduced by 70% to 90%. For 3 ITP patients, a total of 9 immunoapheretic treatments were monitored for reduction in IgG subclasses:

| | |
|---|---|
| $IgG_1$ | 31–68% reduction |
| $IgG_2$ | 25–73% reduction |
| $IgG_3$ | 43–69% reduction |
| $IgG_4$ | 25–68% reduction |

There was no morbidity or mortality associated with the use of the column procedure. Plasma loss was typically low (4–8%), and no plasma replacement was required.

An example of the results from one patient are shown in Table 1 below:

TABLE 1

| column treatment | Circulating Immunoglobulins [%] | | | | | | |
|---|---|---|---|---|---|---|---|
| | IgG total | $IgG_1$ | $IgG_2$ | $IgG_3$ | $IgG_4$ | IgM | IgA |
| 0 | 100 | 100 | 100 | 100 | 100 | 100 | 100 |
| 1 | 23 | 22 | 26 | 23 | 31 | 52 | 51 |
| 2 | 7 | 8 | 8 | 8 | 10 | 23 | 24 |
| 3 | 3 | 4 | 4 | 8 | 7 | 10 | 8 |

The patient in Table 1 received the above described immunoglobulin-depleting column treatment every second day for about 3.5 hours, thereby processing about 8.3 liters of plasma per treatment. The results in Table 1 illustrate the rationale for repeated column treatments. According to literature reports, immunoglobulin is redistributed from the extravascular compartment to the intravascular compartment within 24 hours after removal of plasma immunoglobulin. Therefore, successive column treatments repeated after 24–48 hours are most effective in removing the human subject's body stores of immunoglobulin.

The effect on panel reactivity of the column treatment in Table 1 is shown in Table 2 below:

TABLE 2

| column treatment | panel reactivity |
|---|---|
| 1 before | 98% |
| after | 44% |
| 2 before | 95% |
| after | 38% |
| 3 before | 86% |
| after | 12% |

Combined results from preliminary clinical trials are shown below in Tables 3–5:

TABLE 3

| column treatment | IgG [%] | IgA [%] | IgM [%] |
|---|---|---|---|
| before | 100 | 100 | 190 |
| after | 14 | 32 | 27 |

TABLE 4

| subclass | reduction by column treatment [%] |
|---|---|
| $IgG_1$ | 86 |
| $IgG_2$ | 84 |
| $IgG_3$ | 92 |
| $IgG_4$ | 86 |

Table 5 below shows the reduction in Ig after successive cycles within an individual IA treatment.

TABLE 5

| immuno- apheresis | IgG | | IgA | | IgM | | panel reactivity |
|---|---|---|---|---|---|---|---|
| | mg/ml | % | mg/ml | % | mg/ml | % | % |
| 0. cycle | 8.56 | 100 | 2.99 | 100 | 0.81 | 100 | 89.2 |
| 3. cycle | 4.28 | 50 | 1.99 | 67 | 0.44 | 55 | 75.9 |
| 6. cycle | 2.64 | 31 | 1.38 | 46 | 0.32 | 39 | 67.0 |
| 8. cycle | 1.36 | 16 | 1.02 | 34 | 0.25 | 31 | 5.4 |
| 9. cycle | 1.20 | 14 | 0.96 | 32 | 0.21 | 27 | 2.8 |

Conclusions: The column procedure of the present invention can be used safely for the removal of IgG and IgM from the blood of human patients. Moreover, the column procedure greatly reduces the level of anti-HLA antibodies in sensitized and hypersensitized patients.

EXAMPLE 2

Immunoapheresis combined with cyclophosphamide pulse for transplant to hypersensitized patients.

This renal transplantation study included three female and two male patients between the ages of 25–38 years.

Before entering the study, the patients had between one and four (i.e.: 1, 2, 2, 4, 4) previous kidney transplantations. All of them had panel-reactive-antibodies (PRA) higher than 80% and were awaiting renal transplantation for more than one year as required by the study entry criteria.

The patients were treated with Ig-Therasorb® columns (310 or 150 ml size) before and after transplantation to reduce immunoglobulins and thus PRA's. All columns are adjusted to have about the same binding capacity regardless of column volume. Each patient received between 22 and 59 Ig-Therasorb®-Immunoapheresis treatments including both pre- and post-transplantation procedures. During each procedure, between 5.2 and 9.5 liters of plasma were treated. After an initial series of 3 to 5 treatments patients were given a pulse of cyclophosphamide (750 mg/m$^2$) and high dose IVIG (Gammagard® 0.4 to 1 g/kg BW)). Further on patients were given IVIG after each series of immunoaphereses, and prior to longer apheresis-free intervals.

As of December 1994 four of the five patients had been transplanted, while the remaining patient was awaiting transplantation.

During the pre-transplantation period each patient received between 8 and 27 immunoapheresis (IA) treatments; after transplantation each received between 7 and 45 IA-treatments.

Post-transplant observations as of Dec. 27, 1994:

Patient # 0201 (female, 29 yrs) was transplanted 21 months previously and was off apheresis for 19 months. She had 8 IA-treatments before and 15 IA-treatments after renal transplantation. In total 23 IA-treatments were performed.

Patient # 0202 (male, 33 yrs) was transplanted 16 months previously. He continued on regular IA treatment post-transplant with intervals between IA sessions increasing to about 10 weeks. The patient underwent 59 IA treatments to date.

Patient # 0203 (female, 38 yrs) was transplanted one month previously and underwent post-transplantation IA treatment according to the protocol.

Patient # 0204 (female, 25 yrs) was transplanted six months previously and was off apheresis for three months. She recieved a total of 25 apheresis-treatments (10 pre- and 15 post-transplantation).

Patient # 0205 (male, 33 yrs) was in the pre-transplantation period and awaiting renal transplantation. He had recieved 22 IA-treatments to date.

Renal Transplantation Patients

Number of Immunoapheresis Treatments (IA)

| Pt # | age | IA pre-Tx | IA post-Tx | IA total | Comment |
|---|---|---|---|---|---|
| 0201f | 29 | 8 | 15 | 23 | off IA 19 mo |
| 0202m | 33 | 14 | 45 | 59 | ongoing |
| 0203f | 38 | 27 | 7 | 34 | post Tx |
| 0204f | 25 | 10 | 15 | 25 | off IA 3 mo |
| 0205m | 33 | 22 | N.A. | 22 | awaiting Tx |

Total IgG was typically reduced by about 70 to 90% during the IA-treatment sessions as depicted in FIGS. 6–9 for patients 0201 through 0204.

In the transplanted patients, the grafts had two or more mismatches in the HLA-Antigen profile when compared to recipient plasma prior to any IA treatment. Table 6 below lists the HLA-typing of donor and recipient.

TABLE 6

HLA-Typing in Donor and Recipient

| HLA of | Pt 0201 | Pt 0202 | Pt 0203 | Pt 0204 |
|---|---|---|---|---|
| Recipient | A1, A26, B38(16), B49(21), DR4, DR6 | A3, A28, B7, B27, DR6 | A2, B49(21), B35, cw4cw7, DR5, DR6 | A1, B18, DR2, DR8 |
| Donor | A1, A26, B7, DR2, DR6 | A3, A30, B7, B47, DR6 | A2, A32, 13, B38, DR11, DR13 | A1, A29, B44, B57, DR7, DR8 |

Figure 2:
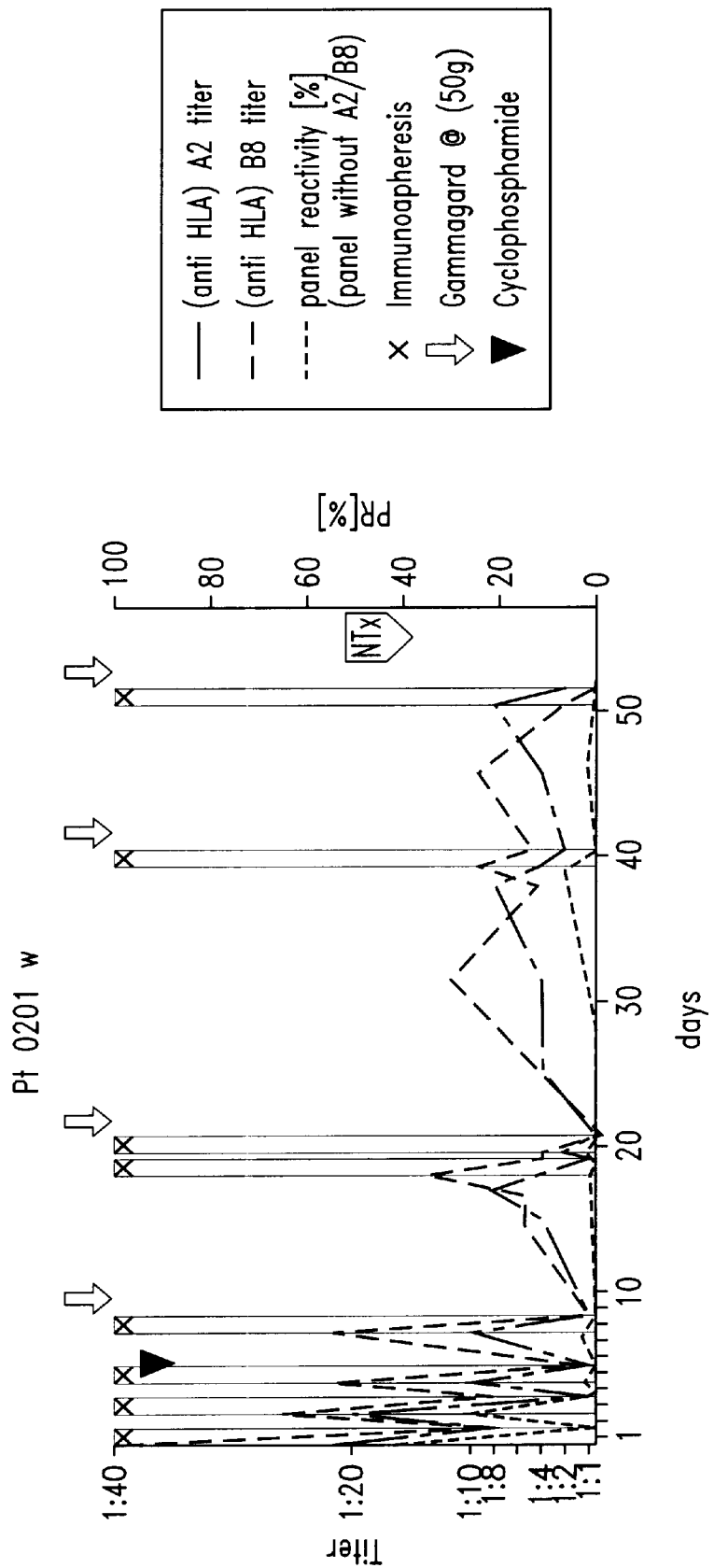
FIG. 2 shows a typical pre-transplantation treatment protocol for the method of the invention.
Figure 3:
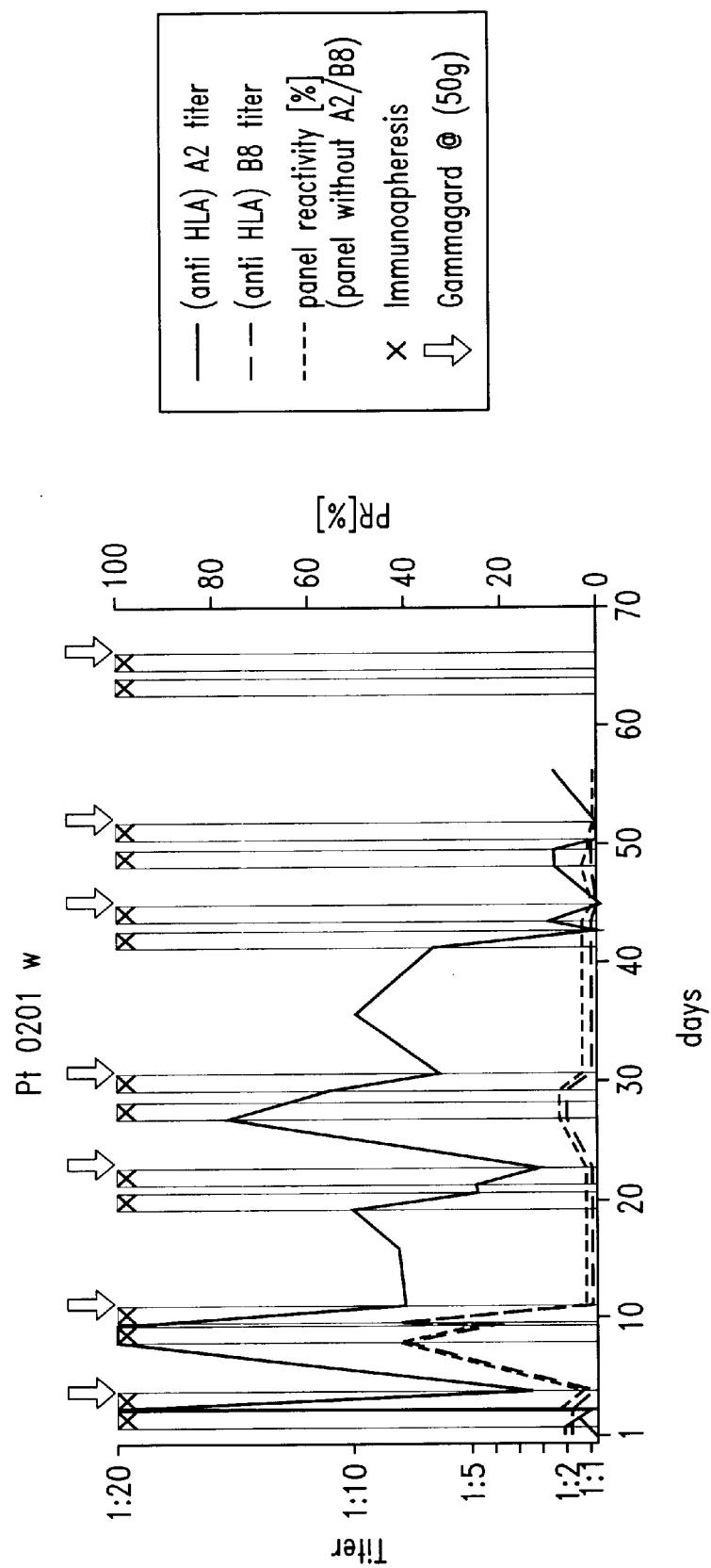
FIG. 3 shows the post-transplantation treatment for the patient of FIG. 2.
Figure 4:
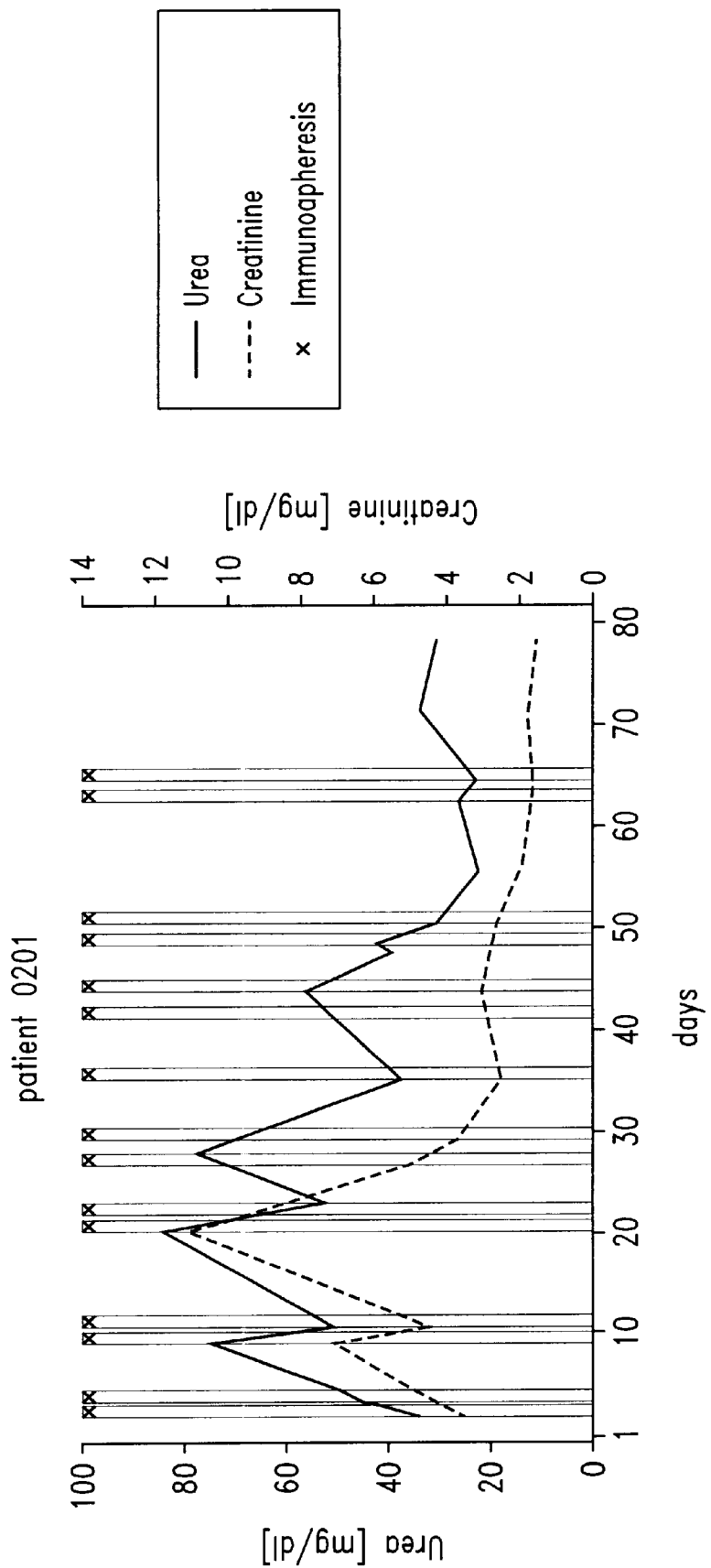
FIG. 4 shows post-transplantation urea and creatinine values for the patient of FIGS. 2 and 3.
Figure 5:
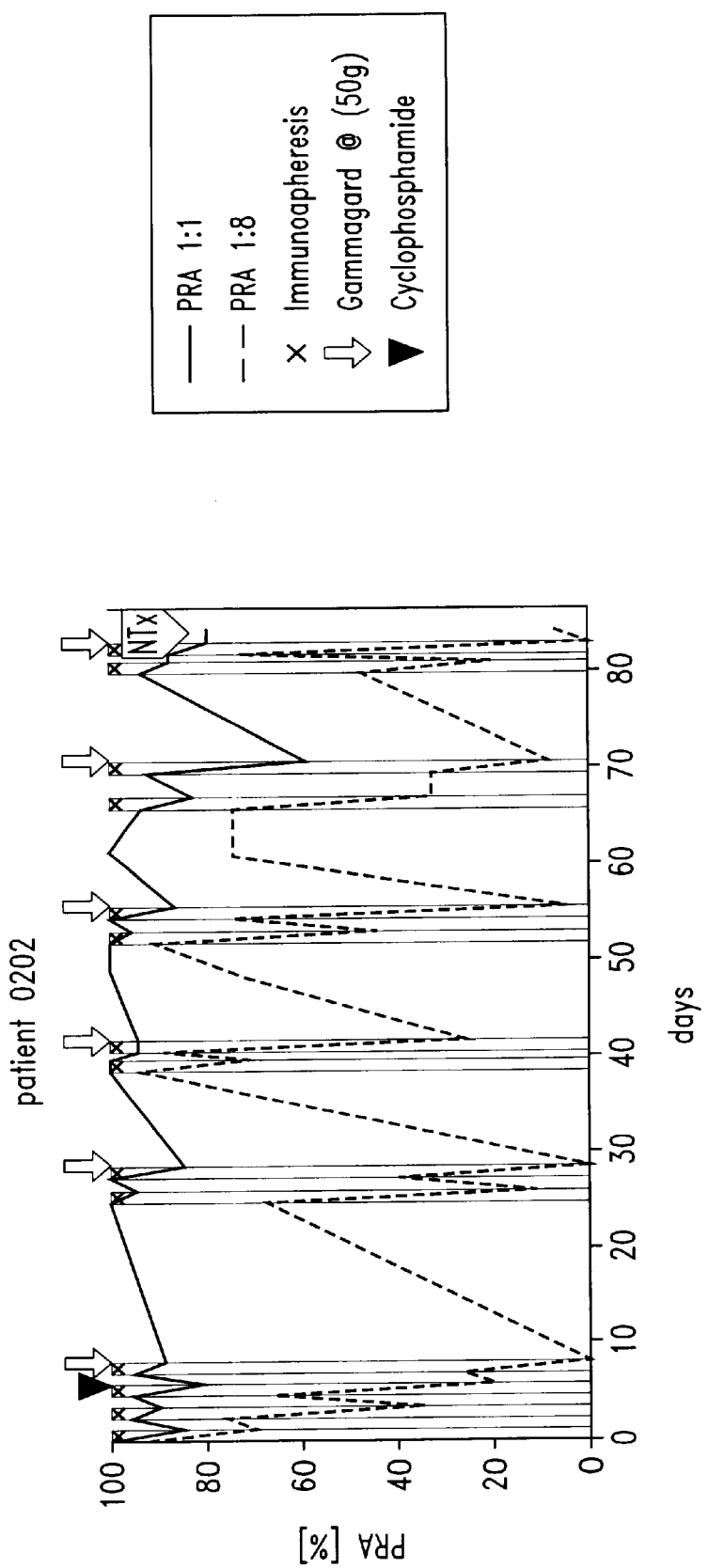
FIG. 5 shows another typical pre-transplantation treatment protocol.
Figure 6:
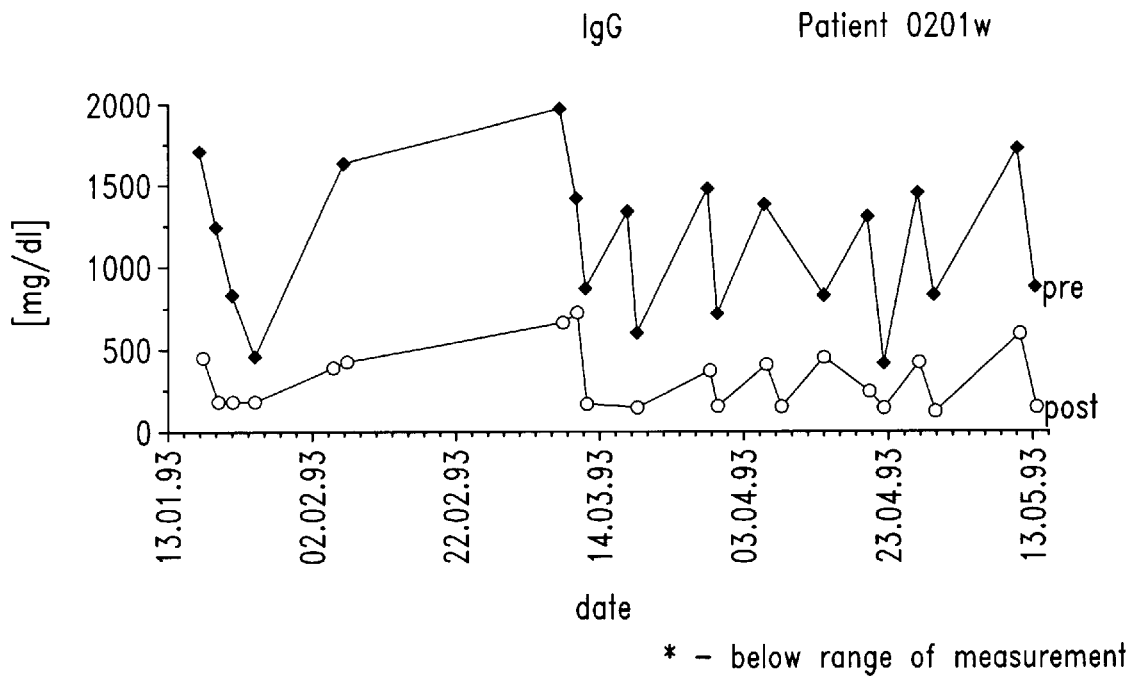
FIG. 6 shows the IgG values for the patient of FIGS. 2 and 3.
Figure 7:
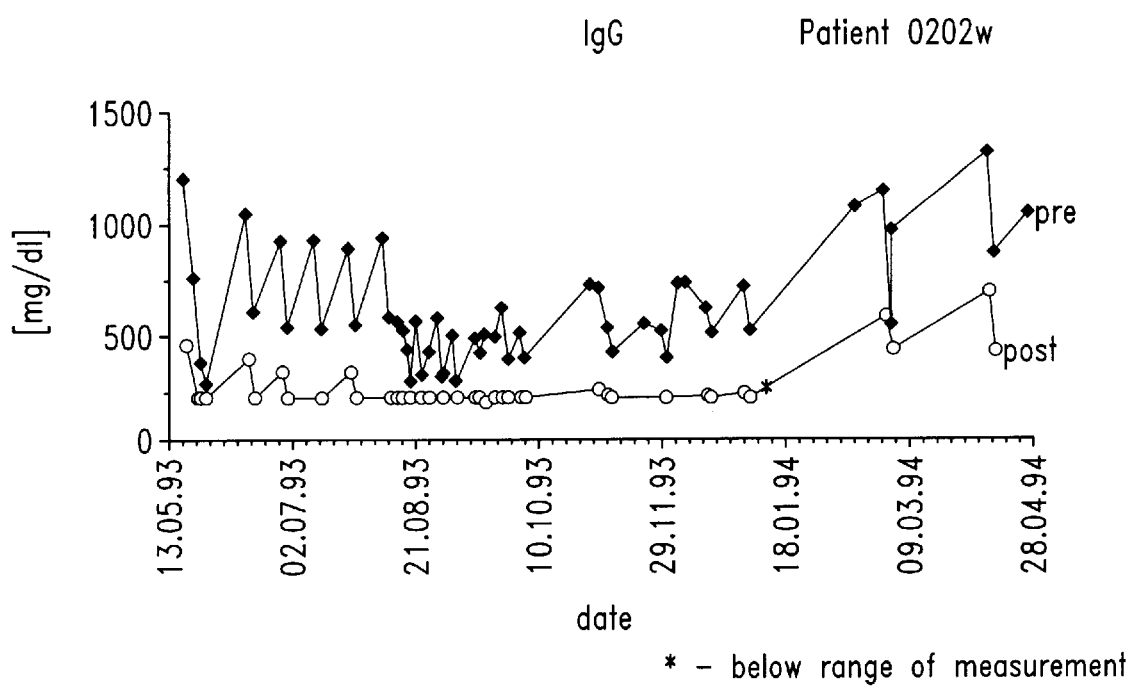
FIG. 7 shows the IgG values for the patient of FIG. 5.
Figure 8:
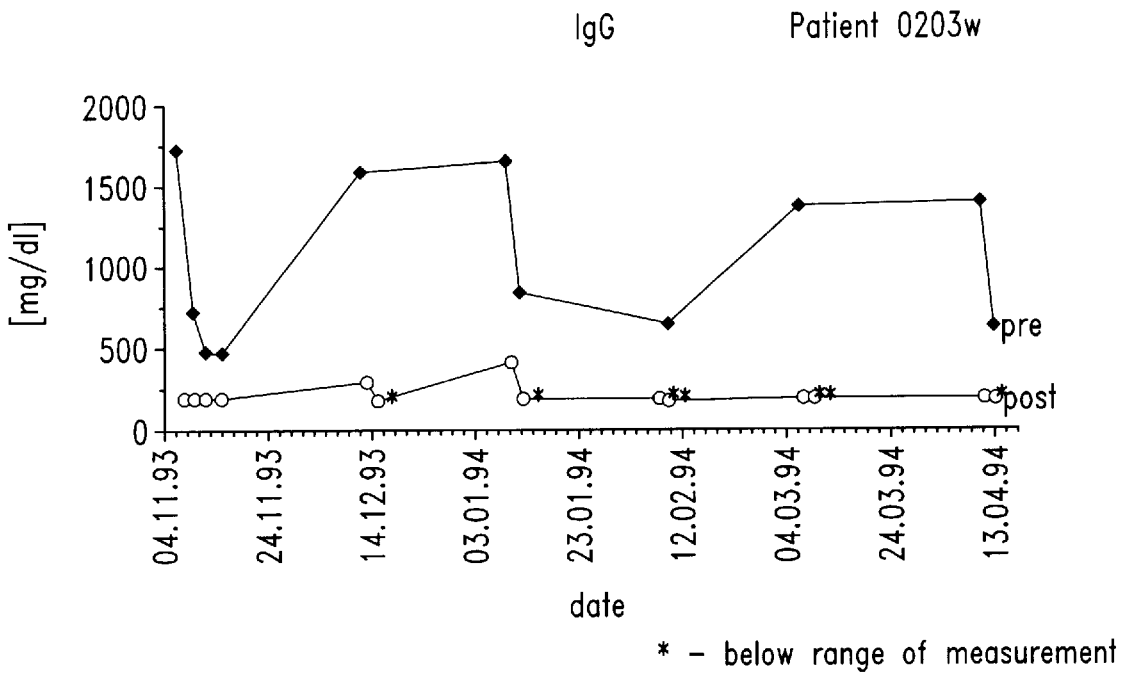
FIG. 8 shows the IgG values for one additional patient treated by the method of the invention.
Figure 9:
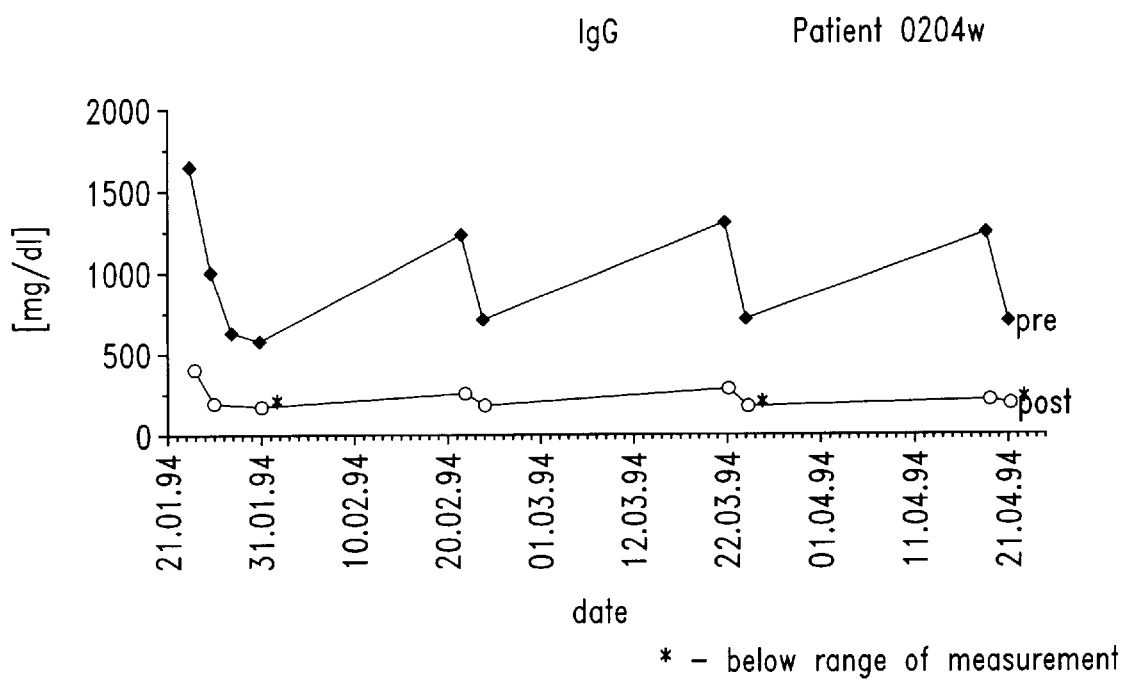
FIG. 9 shows the IgG values for one additional patient treated by the method of the invention.

In FIGS. 2,3 and 5, and in Table 7 below, the influence of Therasorb®-Immunoapheresis on PRA is shown for patients 0201 and 0202.

TABLE 7

Post-transplantation period, patient 0202m

| | | PRA (1:8) | | |
|---|---|---|---|---|
| day | IA# | below 30% | above 30% | creatinine mg/dl |
| 1–60 | 19 | 13 | 6 | 1.19–7.30 |
| 61–120 | 7 | 10 | 0 | 1.36–1.90 |
| 121–180 | 4 | 12 | 1 | 1.48–2.08 |
| 181–240 | 3 | 3 | 3 | 1.55–1.97 |
| 241–300 | 4 | 6 | 1 | 1.97–2.04 |

In consecutive Therasorb®-IA, PRA can be reduced significantly, concomitant with the reduction of IgG.

In patients with very high titre-anti-HLA-antibodies (0202m) the effect of Therasorb®-IA may only be revealed by analysing PRA's in diluted samples.

Both patients recieved a bolus infusion of cyclophosphamide after Therasorb®-IA # 3 and (IVIG)Gammagard® after Therasorb®-IA # 4.

Immediately after transplantation a rise in PRA-concentration was evident, indicating a "boostering effect" exerted by the graft in the recipient.

Removal of anti-HLA-antibodies by repeated IA treatment immediately post-transplantation is therefore believed to be very critical for the survival of the graft in these patients. Removal of antibodies was performed according to protocol in the first two months following transplantation and thereafter guided by serum creatinine-levels of the patients (FIG. 5 and Table 7).

Some patients may need longer periods of IA treatment post-transplantation, but it is expected that for each patient intervals between IA treatments can be steadily increased, and finally the patient can go off IA without experiencing hyperacute or acute rejection of the transplanted organ.

EXAMPLE 3

Production and Viral Inactivation of Anti-human Ig and Antihuman LDL Antibody Solutions The production of immunized sheep plasma was carried out under Good Manufacturing Practices approved by the local government of Heidelberg, Germany. The flock of healthy male sheep was kept in a special paddock isolated from other animals. Their natural grass feed was supplemented by the provision of additional nutritional feed without animal meal. All sheep were examined on a routine basis by a qualified veterinary surgeon, who followed written procedures for care of the animals. The incoming new sheep were first placed in quarantine for a minimum of three weeks and tested serologically (antibody search for *Brucella melitensis*, Leptospira, *Listeria monocytogenes*, and Border Disease virus). An additional test for antibodies against Maedi Visna virus was done every six months for a total of three tests.

Polyclonal antisera directed against human immunoglobulin were raised by injecting sheep with a human IgG immunogen prepared from a pooled human plasma fraction of immunoglobulin (Gammagard S/D™, Baxter Hyland) together with complete Freund's adjuvant.

Polyclonal antisera directed against human LDL were raised by injecting sheep with an immunogen composed of complete Freund's adjuvant and affinity-chromatography purified LDL from the plasma of human subjects. The subjects who donated LDL were rigorously screened, and monitored after donation, for major blood born viruses. Moreover, the holding period between the collection of LDL and its first use was a minimum of 6 months. Thus, any donated LDL from subjects who tested positive for virus during this time could be rejected before release of product.

The animals received initial and booster injections of immunogen. Plasma was obtained from the immunized animals by routine plasmapheresis using a cell separator device equipped with sterile, pyrogen-free disposable tubing sets. The sheep plasma was anti-coagulated with ACD. The disposable tubing sets were primed with sterile, pyrogen-free sodium chloride solution. Plasma was collected via a closed tubing system in sterile, pyrogen-free transfer packs (Baxter/Fenwal) and immediately frozen at about −20° C. (range −18° C. to −30° C.). The plasma was stored frozen until the next processing step.

Alternatively, monoclonal antibodies could be raised against human immunoglobulin by first injecting mice with an appropriate antigen such as a human kappa or lambda light chain. Monoclonal antibodies against human LDL could be raised by first injecting mice with a purified preparation of LDL. The spleen cells of the immunized mice could then be fused with myeloma cells to form antibody-producing hybridomas (Kohler, G. and Milstein, C., 1975 *Nature* 256:495–497).

In order to select for monoclonal antibodies to couple to a column useful for preparing a subject for a pig organ transplant, the secreted anti-human Ig monoclonal antibodies could be screened in a porcine endothelial cell ELISA-type assay as follows: (1) multiwell tissue culture plates would be prepared with a coating of porcine endothelial cells; (2) the porcine endothelial cells would be incubated with human immunoglobulin to allow human anti-pig antibodies to bind to the pig cells; (3) human immunoglobulin which does not bind to pig cells would be rinsed away; (4) conditioned media from individual monoclonal hybridomas would be incubated in the wells to allow monoclonal antibodies to bind to the human anti-pig antibodies, which in turn would be bound to the pig cells in the wells; (5) markers for the monoclonal antibodies would be added such as fluorescein-conjugated sheep anti-mouse antibodies; (6) the wells which fluoresced brightly would be considered positive for containing a monoclonal antibody which binds to human immunoglobulin, which in turn binds to pig cells.

Secreted anti-human LDL antibodies could be screened in an ELISA based on LDL-bound ELISA plates.

In this way, one or more appropriate monoclonal antibodies would be identified for large-scale production. These monoclonal antibodies could then be purified by affinity chromatography followed by ion-exchange chromatography, and then coupled to the column matrix material as described below.

Once an appropriate monoclonal antibody is identified and sequenced, it would then become possible to produce recombinant antibodies such as multiple- or single-chain antibodies. In another embodiment of the invention, these recombinant antibodies could be coupled to the column matrix material. Recombinant multiple-chain antibodies could be produced according to the methods described in U.S. Pat. No. 4,816,397 (Boss, et al.; herein incorporated by reference). Recombinant antibodies could be produced according to the methods described in U.S. Pat. No: 4,946,778 (Ladner, et al.; herein incorporated by reference).

When the antibodies are produced as monoclonals or by genetic engineering, it is possible to closely control their sterility. However, when the antibody to be coupled to the column is raised in an animal, it is especially important to assure that any viruses present in the animal serum are inactivated.

In the case of polyclonal antisera raised in sheep, described above, the following procedures were carried out under aseptic conditions using sterile and pyrogen-free instruments, plastic products, and solutions. The plasma pool was recalcified by addition of 1–10~1 CaCl2 solution (1 mol/l) per ml of serum, and stirring at room temperature overnight. The plasma clot was then separated by centrifugation.

The animal serum was prepared for virus-inactivating heat treatment by mixing with a stabilizer consisting of saccharose (30% w/w) and ascorbic acid (5 mmol/l). The stabilized serum was then filled into empty bags, heated to at least 60° to about 62° C., and held at this temperature for at least 10 hours. The heat treated serum was filtered into empty bags through a 20 gm transfusion filter. The filled bags were aseptically sealed, labeled and stored at –20° C. (range –18°–30°).

This viral inactivation process, as well as subsequent processes, were validated by spiking with three model viruses prior to each production step, and then assaying for any remaining infective virus. These 3 model viruses (human polio virus type 2, human adenovirus type 2, and ovine maedi visna virus) represented a range of human and animal viruses with different physicochemical properties. The maedi-visna virus of sheep is a lentivirus (retrovirus). The adenoviruses are large DNA viruses and, like other unenveloped viruses tend to be more resistant than enveloped viruses to physico-chemical inactivation. Poliovirus is a small RNA virus that is particularly resistant to many physico-chemical processes, including the use of low pH buffers, which are used at several steps below. In processes involving human blood products, a herpesvirus was spiked in replacement for the adenovirus.

Specific inactivation studies in human blood products were also conducted for HIV.

After the virus inactivation step, the serum pool was again frozen as above. The next step in processing of the serum pool involves circulation over two glass columns known as the pre-column and the working column. In the case of anti-LDL serum, the pre-column contains Sepharose™ coupled to human Ig and human albumin, and the working column is coupled to human LDL. In the case of anti-human Ig serum, the pre-column contains Sepharose™ coupled to human albumin and the working column is coupled to human IgG.

EXAMPLE 4

Preparation of Pre-Column and Working Columns

All of the steps were conducted under aseptic conditions.

Pre-column for anti-LDL: Human serum albumin and IgIV (Gammagard®, Baxter Hyland Division) were coupled to Sepharose™ essentially as described below.

Pre-column for anti-human Ig: Human serum albumin was coupled to Sepharose™ essentially as described below.

Working column for anti-LDL: LDL was obtained by affinity chromatography from the plasma of subjects as described above, and coupled to Sepharose™ as described below.

Working column for anti-human Ig: A preparation of pooled human immunoglobulin (Gammagard®, Baxter, Hyland Division) was dissolved in buffer (140 g Gammagard®/100 ml buffer). The dissolved Gammagard® was subjected to ultrafiltration to remove glycine, because it was found that glycine impairs the chromatographic separation of IgG from albumin. Gammagard® typically contains, per 10 g lyophilisate, 4500 mg glycine/100 m. The goal was to reduce the glycine content to less than 960 mg/l, which required six ultrafiltration steps. For ultrafiltration, the Gammagard® was diluted with sterile buffer to 5000 ml, the solution was concentrated to 1000 ml, and the steps were repeated 5 more times. Then the Gammagard® solution was passed through a 0.2~m sterilizing filter.

Human IgG was isolated from Gammagard® using two gradient steps of ion exchange chromatography (300 ml Q-Sepharose™ Fast Flow packed into a XK50/30 column; column height ca. 14 cm, diameter 5 cm; Pharmacia) at 2–8° C. The purity of the isolated IgG was tested using SDS gel electrophoresis.

The next step was to couple the IgG to the column matrix material. However, it was discovered that TRIS and residual glycine in the purified IgG solution impaired the coupling of IgG to the column matrix material. To overcome this problem, an 11-step ultrafiltration procedure was devised to reduce the TRIS content to less than 211 $\mu$g/l and the glycine content to less than 35 $\mu$g/l. The volume of the IgG solution was brought to 5000 ml with pH 9 sterile sodium carbonate buffer. The solution was concentrated by ultrafiltration under constant stirring to 1000 ml, and the procedure was repeated 10 times. After the 10th step, the solution was reduced to 2000–2500ml. The solution was then analyzed for protein, TRIS, and glycine content, and sterile filtered in an isolator. The solution was at pH 9 at this step.

Alternatively, a mix of human immunoglobulins such as IgG and IgM could be coupled to the sterile matrix.

The matrix material was sterilized, activated, and coupled to the appropriate protein solution as described below for preparation of the therapeutic columns.

Results: At least 15 g (range 10–20 g) human IgG was coupled to 350 g (range 300–400 g) of matrix material in order to achieve a sufficient binding capacity for the working column.

EXAMPLE 5

Sterile Purification of Anti-Human Ig Antibodies.

The pasteurized serum pool from Example 1 was thawed and circulated over two glass columns, one containing Sepharose CD4B coupled to albumin (pre-column) and the other containing Sepharose CL4B coupled to IgG (working column).

The serum loading and column washing process was carried out by a closed automated chromatographic system (BioPilot™ system, Pharmacia) in a class 100,000 clean room at an ambient temperature of 2°–8° C. The BioPilot™ system was under permanent bioburden control, CIP-runs (cleaning in place procedure) were done routinely, and during longer stand-times the pre- and working columns were filled with 0.1% sodium azide solution.

The connections from the system to containers of the sheep serum, the sterile buffers, and the sterile filters were made under aseptic conditions with specially designed disposable, sterile, and pyrogen-free plastic tubing sets.

At the beginning of each run, the serum can be diluted up to 5000 ml with sterile PBS buffer. The serum solution was then passed automatically over the pre-column, followed by automatic passage over the working column.

Once the desired antibodies had bound to the working column, and the undesired substances had flowed out of the column, the desired antibodies were eluted from the working column. Preferably, after 3000–8000 ml citrate elusion buffer had been passed, the collected eluate contained 70–100% of the antibodies originally loaded onto the columns.

Optimal results were achieved only after the preferred citrate elusion buffer was discovered. Laboratory experiments using various elusion buffers are shown in Tables 8–10 below:

TABLE 8

COMPARISON OF THE AMOUNT OF SHEEP-ANTIBODY USING DIFFERENT ELUTION BUFFERS FOR AFFINITY CHROMATOGRAPHY
Laboratory data with experimental working columns:

| elusion buffer | pH | eluted antibody mg | % |
|---|---|---|---|
| a) LDL-Therasorb working column | | | |
| 0.1M NaAc/0.15M NaCl | 2.8 | 93 | 100 |
| 0.13M NaCitrate | 2.2 | 108 | 116 |
| 0.2M Glycine/HCl | 2.8 | 93 | 100 |
| b) IG-Therasorb working column | | | |
| 0.1M NaAc/0.15M NaCl | 2.8 | 33 | 100 |

TABLE 8-continued

COMPARISON OF THE AMOUNT OF SHEEP-ANTIBODY USING DIFFERENT ELUTION BUFFERS FOR AFFINITY CHROMATOGRAPHY
Laboratory data with experimental working columns:

| elusion buffer | pH | eluted antibody mg | % |
|---|---|---|---|
| 0.13M NaCitrate | 2.2 | 47 | 142 |
| 0.2M Glycine/HCl | 2.8 | 41 | 124 |

TABLE 9

INFLUENCE OF THE PH ON THE AMOUNT OF ELUTED ANTIBODY
Laboratory data with experimental working columns:

| elution buffer | pH | eluted antibody mg | % |
|---|---|---|---|
| a) LDL-Therasorb working column | | | |
| 0.1M NaAc/0.15M NaCl | 2.8 | 93 | 100 |
| 0.1M NaCitrate | 2.1 | 100 | 107 |
| 0.1M NaCitrate | 2.2 | 108 | 116 |
| 0.1M NaCitrate | 2.4 | 101 | 108 |
| 0.1M NaCitrate | 2.6 | 94 | 100 |
| 0.1M NaCitrate | 2.8 | 77 | 83 |
| b) IG-Therasorb working column | | | |
| 0.1M NaAc/0.15M NaCl | 2.8 | 33 | 100 |
| 0.1M NaCitrate | 2.1 | 51 | 155 |
| 0.1M NaCitrate | 2.2 | 59 | 181 |
| 0.1M NaCitrate | 2.4 | 52 | 160 |
| 0.1M NaCitrate | 2.6 | 49 | 148 |
| 0.1M NaCitrate | 2.8 | 42 | 127 |

TABLE 10

INFLUENCE OF THE SODIUM CITRATE CONCENTRATION ON THE AMOUNT OF ELUTED ANTIBODY
Laboratory data with experimental working columns; IG-Therasorb working column

| elution buffer | pH | eluted antibody mg | % |
|---|---|---|---|
| 0.10M NaAc, 0.15M NaCl | 2.8 | 33 | 100 |
| 0.025M NaCitrate | 2.2 | 49 | 148 |
| 0.050M NaCitrate | 2.2 | 51 | 155 |
| 0.100M NaCitrate | 2.2 | 50 | 152 |
| 0130M NaCitrate | 2.2 | 52 | 158 |
| 0.150M NaCitrate | 2.2 | 44 | 133 |
| 0.200M NaCitrate | 2.2 | 28 | 85 |

Results: Glycine buffer was found to be unsuitable because the glycine amino groups in the eluted antibody solution coupled to the activated matrix material in the subsequent coupling step. Therefore, with the glycine buffer, a time-consuming dialysis step was required to exchange the glycine for carbonate. The acetate buffer was also unsuitable. Using either glycine buffer or acetate buffer, the amount of antibody eluted from the working column decreased over time, making the process relatively inefficient and costly. However, it was discovered that a citrate buffer could efficiently elute the desired antibodies while retaining their binding capacity. Moreover, the presence of citrate did not adversely affect subsequent production steps. The preferred elusion buffer was found to be 0.13 M sodium citrate at a pH of 2.2. Compared to the acetate buffer, the amount of eluted antibody using the optimal citrate buffer was about 20–40% higher.

During the elusion procedure, eluted antibodies were passed through sterilizing filters (0.2 pM) on-line and collected into disposable, sterile, and pyrogen-free receiving bags and stored at 2–8° C.

In order to concentrate the antibody solutions, an ultra-filtration step was carried out in a class 100,000 clean room with a 10,000 kD membrane (Omega series, low binding polyethersulfone, Filtron Technology Corporation). Typically, the antibody solution was concentrated about 20–80 fold, or from about 50–200 liters down to about 2.5 liters. Samples of the processed antibodies were taken under aseptic conditions for in-process monitoring after the ultra-filtration step.

At this point, the concentrated eluate contained about 74–97% of the antibodies originally bound to the column.

EXAMPLE 6

Preparation of Sterile Pyrogen Free Column Matrix Material

The column matrix material was rendered sterile and pyrogen-free by a series of pre-rinses, followed by steam sterilization. The procedure was carried out inside a sterilized isolator.

Approximately two days before the start of this procedure, an agarose bulk material (Sepharose-CL4B) was filled aseptically into a sterile and pyrogen-free 5 liter beaker for settling by gravity overnight. On the second day, the volume of the Sepharose™ was checked for a minimum of 2100 ml settled gel (=6 bottles @ 350 ml) per one 5 liter beaker. The Sepharose™ volume was regulated aseptically, and allowed to settle again if necessary.

Working within the isolator, each batch of Sepharose™ was rinsed with a total volume of minimum 21 liters of sterile and pyrogen-free water, in steps of 4500 ml each. Between each step, the Sepharose™ was completely dried by vacuum. The final rinsed suspension was then filled into 500 ml bottles and closed with rubber stoppers.

Samples were taken for bioburden determination. [Bioburden testing was conducted at several points in the production process at H30, FIG. 1.] Bioburden testing was required to show no enteric bacteria, no *Pseudomonas aeruginosa*, and no *Staphylococcus aureus*; an alert limit of 1 aerobe growing bacterium/g or ml of sample was set. The bottles were evacuated under aseptic conditions using a manual vacuum pump, and closed tightly with metal caps.

The bottles of rinsed Sepharose™ were then steam sterilized within 72 hours after the above rinsing step. The steam sterilization was conducted using a validated steam auto-clave at 115° C. for a minimum of 20 minutes at <2 bar. The cycle time was regulated automatically to reach an $F_0$ value of 6. After steam sterilization, samples were taken for bioburden determination and testing for pyrogenicity. The bioburden test was required to show a maximum of 1 colony-growing organism/100 ml. The pyrogenicity test (Limulus-amoebocytelysate test) was based on the ability of endotoxins to cause egg-white gelling by an amoebocyte extract. The Lowry eggwhite test then was used to quantitate the endotoxin amount colorimetrically at 660 nm. The pyrogen content was required to be below 0.25 EU/ml.

EXAMPLE 7

Activation of Matrix Material and Coupling of Antibodies

This procedure and other procedures identified above and in FIG. 1 were carried out inside a sterilized isolator. One of the main difficulties is using isolators for aseptic work is the process of sterilizing the inside of the isolator itself before beginning the aseptic procedure. A vapor generator (La Calhene, France), heats peracetic acid (PAA) to form a vapor, and thereby fume sterilizes the isolator. This method is dry but slow-acting, due to lower chemical and water activity and vapor/air mixing problems. Fortuitously, it was discovered that a vapor nebulized mist could simplify the sterilization of the isolator by reducing the time and operator effort required. In the method of the present invention, the liquid sterilant was nebulized into the isolator in the smallest amount necessary to provide a saturated vapor and a surface condensation. During the introduction and exposure, the sterilant was circulated within the isolator. The nebulizer operated by breaking up liquid in a container through input of energy at ultrasonic frequencies. The nebulizer used was Ultra Neb™ 99 (DE VILBISS). The container of the nebulizer was filled with 200–210 ml of peracetic acid, and the tubing of the nebulizer was connected to the entrance at the backside of the isolator The ventilator was installed inside the isolator at the clutch. The isolator was then loaded with the materials required for the next step according to a validated loading pattern. The air out tube was connected to the used air system. The nebulization process was begun, with a pressure inside the isolator of not more than 1 mm Hg. The nebulization was stopped when the PAA content of the nebulizer was reduced to 160 ml (nebulization uptake of 40–50 ml). This was followed by a holding time of at least 10 minutes. After the holding period, the isolator was flushed by switching on the ventilator of the isolator to isolator overpressure (approximately 4–5 mm Hg) and opening the outlet vent. For each individual isolator, a minimum flushing period was validated (typically a minimum of 80–110 minutes).

A stainless steel activation vessel was used to activate 1800 ml Sepharose™CL4B in one batch within an isolator. The activation vessel had to be sterilized prior to use. At first, the stainless steel vessel was heat sterilized a 250° C.–280° C. for a minimum of 2 hours. However, this treatment created stresses between the scinter and the body of the activation vessel, which led to loose or thin spots between the scinter and the bottom. From this treatment, the material of the activation vessel wore out quickly. Gas nebulization sterilization was used instead.

An isolator was installed in a class 100,000 clean room. All materials and labware were installed in the isolator, the inside of which was then sterilized by the ultrasonic nebulization process described above. A waste container filled with calcium hypochlorite for CnBr inactivation was installed outside the isolator. Pall™ sterile filter units were sterilized and installed on the isolator. One filter was used for filtration of sterile pyrogen-free water into the isolator, and the other was used for removal of waste liquids into the outside waste container.

Working inside the isolator, the Sepharose™ was rinsed three times with sterile, pyrogen-free water, and then rinsed and resuspended in 60% acetone/water. Next, the Sepharose was activated with CnBr and triethylamine (TEA) solution. CNBr: 14–15 g cyanogen bromide per 96 ml acetone. For activation within the stainless steel vessel, 1800 ml was required. TEA: 30 ml triethylamine (analytical grade, Merck) in 66.2 ml of 87% acetone. The Sepharose™/acetone/water slurry was cooled to −18° C., and the CNBr solution (about 580–650 ml) was added in a continuous flow over 1 minute. Then the TEA solution (about 580–650 ml) was added in a continuous flow over 2 minutes. The temperature of −10° C. was reached when the exothermic reaction was finished (approximately 45 seconds after finishing the TEA addition). One minute after the TEA addition, the acetone/HCl solution was added. Acetone/HCl: 392 ml sterile, pyrogen-free water, 16.3 ml 5 N HCl, 408 ml acetone. Several bottles of Sepharose™ were activated one at a time in this fashion. Activated Sepharose™ was used for coupling within 3 hours, preferably as soon as possible.

A cyanate ester determination was performed on the activated Sepharose™ using the Spectroquant™ test kit (Merck) before adding the concentrated antibodies to test the efficiency of the chemical activation.

After activation, the Sepharose™ was quickly rinsed in the activation vessel five times in sterile, pyrogen-free water. This step had to be performed quickly in order to avoid hydrolysis of active groups. The sterile filtered antibody solution was then transferred into the activation vessel and stirred for 2 hours. After 2 hours the Sepharose™ suspension was then rinsed 2 times by alternating solutions of pH 2.8 (range 2.2–3.0) and PBS. The Sepapharose™ was gently resuspended in PBS and repeatedly rinsed using a total of 60 (range 50–200 liters) of 0.9% NaCl per one activation vessel batch (about 1800 ml Sepharose™). The antibody coupled SepharoseTm bulk was then filled into sterile bottles and capped with a metal cap. The bottles were stored at 2–8 ° C. until the next production step. It was found that the bottles could be stored up to 12 weeks.

The used filters were tested for integrity. [Filter integrity tests were performed several times in the production process, namely at H17 and H31]. After finishing the activation and coupling, the suspension supernatant was subjected to another cyanide test for residual cyanide.

Next, additional rinsing with sterile 0.9% NaCl was carried out to reach an uncoupled protein content in the supernatant below 10 ng per ml The amounts of bound and unbound protein were determined by standard methods. Using the above procedures, it was possible to obtain at least 50–100 g of antibody coupled to 1800 ml Sepharose™ (range 1800–2000 ml).

Each batch was assayed for protein content using the BCA (bicinchoninic acid) reagent and absorption at 562 nm (Smith, et al., *Anal Biochemie* 1985).

EXAMPLE 8

Finishing of Final Product

Glass column housings with glass sinter were cleaned, dried, silanized, and depyrogenated, and then fitted with their connection sets inside a sterilized isolator.

The washed, protein-coupled Sepharose™ was filled into the glass column housings inside the sterilized isolator. Samples were taken for heavy metal analysis, particle analysis, pyrogenicity, and sterility tests.

What is claimed is:

1. A method to ameliorate hyperacute or acute rejection of a human donor organ transplanted to a human recipient, comprising:
    (a) providing a sterile and pyrogen-free column coupled to anti-human immunoglobulin antibodies, wherein the pyrogen content of the column matrix material is below 0.25 EU/mL,
    (b) passing plasma of the human recipient over the column under conditions which effect the binding of said anti-human immunoglobulin antibodies to immunoglobulin in the recipient's plasma, thereby removing at least 50% of the immunoglobulin from said plasma, and recovering a column effluent, and
    (c) reinfusing said effluent to the recipient, and thereby ameliorating hyperacute or acute rejection of a human donor organ transplanted to the recipient.

2. The method of claim 1 wherein the coupled anti-human immunoglobulin antibodies are selected from the group consisting of polyclonal antibodies, monoclonal antibodies, and recombinant antibodies.

3. The method of claim 2 wherein the antibodies are recombinant double-chain or recombinant single-chain antibodies.

4. The method of claim 2 wherein the antibodies coupled to the column specifically bind to epitopes on a member of the group consisting of human lambda light chain, human kappa light chain, human gamma heavy chain, and human mu heavy chain.

5. The method of claim 2 wherein the antibodies coupled to the column specifically bind to epitopes on anti-Human Leucocyte Antigen antibodies.

6. The method of claim 1 wherein said immunoglobulin which is bound by the antibodies coupled to the column is selected from the group consisting of IgG and IgM.

7. The method of claim 1 wherein said step (b) further comprises the passing of at least two plasma volumes of the recipient over the column.

8. A method to ameliorate hyperacute rejection reaction which would normally occur in a human recipient of a human donor organ when the recipient has cytotoxic anti-Human Leucocyte Antigen immunoglobulin against antigens in the donor organ, said method comprising the consecutive steps of:
    (a) providing a sterile and pyrogen-free column coupled to anti-human immunoglobulin antibodies, wherein the pyrogen content of the column matrix material is below 0.25 EU/mL,
    (b) passing plasma of the human recipient over the column under conditions which effect the binding of said anti-human immunoglobulin antibodies to immunoglobulin in the recipient's plasma, thereby removing at least 50% of the immunoglobulin from said plasma, and recovering a column effluent,
    (c) reinfusing said effluent to the recipient,
    (d) repeating steps (b) and (c) at least two times,
    (e) transplanting to the recipient said human donor organ, and
    (f) repeating steps (b) and (c) at least six times in the two weeks following transplantation.

9. The method of claim 8 further comprising, after step (d), administering a pulse of an immunosuppressive agent to the recipient.

10. The method of claim 9 wherein said immunosuppressive agent is selected from the group composed of a cytotoxic agent, an anti-mitotic agent, an antibody directed against lymphocytes, and a vaccine directed against immunocompetent cells.

11. The method of claim 10 wherein said immunosuppressive agent is cyclophosphamide.

12. The method of claim 8 further comprising, after step (d), administering intravenously to the recipient a preparation of normal human immunoglobulin.

13. The method of claim 8 further comprising administering an immunosuppressive agent after step (e).

14. A method to ameliorate hyperacute or acute rejection of a human donor organ transplanted to a human recipient, comprising:
  (a) providing a sterile and pyrogen-free column coupled to anti-human immunoglobulin antibodies, wherein the column is sterilized at a temperature of 115° C. for a minimum of 20 minutes at less than 2 bar;
  (b) passing plasma of the human recipient over the column under conditions which effect the binding of said anti-human immunoglobulin antibodies to immunoglobulin in the recipient's plasma, thereby removing at least 50% of the immunoglobulin from said plasma, and recovering a column effluent, and
  (c) reinfusing said effluent to the recipient, and thereby ameliorating hyperacute or acute rejection of a human donor organ transplanted to the recipient.

15. The method of claim 14 wherein the coupled anti-human immunoglobulin antibodies are selected from the group consisting of polyclonal antibodies, monoclonal antibodies, and recombinant antibodies.

16. The method of claim 15 wherein the antibodies are recombinant double-chain or recombinant single-chain antibodies.

17. The method of claim 15 wherein the antibodies coupled to the column specifically bind to epitopes on a member of the group consisting of human lambda light chain, human kappa light chain, human gamma heavy chain, and human mu heavy chain.

18. The method of claim 15 wherein the antibodies coupled to the column specifically bind to epitopes on anti-Human Leucocyte Antigen antibodies.

19. The method of claim 14 wherein said immunoglobulin which is bound by the antibodies coupled to the column is selected from the group consisting of IgG and IgM.

20. The method of claim 14 wherein said step (b) further comprises the passing of at least two plasma volumes of the recipient over the column.

* * * * *